(12) United States Patent
Kumar et al.

(10) Patent No.: US 9,970,372 B2
(45) Date of Patent: May 15, 2018

(54) METHOD OF DIAGNOSING AN EXHAUST GAS SENSOR

(71) Applicant: Ford Global Technologies, LLC, Dearborn, MI (US)

(72) Inventors: Pankaj Kumar, Dearborn, MI (US); Imad Hassan Makki, Dearborn Heights, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 1128 days.

(21) Appl. No.: 14/180,594

(22) Filed: Feb. 14, 2014

(65) Prior Publication Data

US 2015/0233316 A1 Aug. 20, 2015

(51) Int. Cl.
| | | |
|---|---|---|
| *F02D 41/00* | (2006.01) | |
| *F02D 41/14* | (2006.01) | |
| *G01N 33/00* | (2006.01) | |

(52) U.S. Cl.
CPC ....... *F02D 41/1495* (2013.01); *G01N 33/007* (2013.01)

(58) Field of Classification Search
CPC .......................... F02D 41/1495; G01N 33/007
See application file for complete search history.

(56) References Cited

U.S. PATENT DOCUMENTS

| | | | |
|---|---|---|---|
| 6,209,385 B1 | 4/2001 | Silvis | |
| 6,453,663 B1 * | 9/2002 | Orzel | F01N 3/0842 123/690 |
| 2013/0245919 A1 | 9/2013 | Kumar et al. | |

FOREIGN PATENT DOCUMENTS

WO 9749978 A1 12/1997

OTHER PUBLICATIONS

Kumar, P. et al., "A low-dimensional model for describing the oxygen storage capacity and transient behavior of a three-way catalytic converter," Chemical Engineering Science Journal, vol. 73, pp. 373-387, 2012, 15 pages.
"Lamda Calculation—The Brettschneider Equation, general principles and methods, and its use with alternate fuels," Bridge Analyzers, Inc., White Paper No. 9, Rev. 021007A, Jun. 8, 2003, Alameda, CA, 4 pages.

* cited by examiner

*Primary Examiner* — Hung Q Nguyen
(74) *Attorney, Agent, or Firm* — Julia Voutyras; McCoy Russell LLP

(57) ABSTRACT

Embodiments for an engine exhaust are provided. In one example, a method comprises categorizing each respective concentration of a plurality of exhaust gas constituents measured by a gas analyzer into one of oxidants or reductants, the gas analyzer receiving exhaust gas flow from an engine. The method also includes determining an exhaust air-fuel ratio based on the categorized concentrations and validating output from an exhaust gas sensor receiving exhaust gas flow from the engine based on the determined exhaust air-fuel ratio.

19 Claims, 4 Drawing Sheets

METHOD OF DIAGNOSING AN EXHAUST GAS SENSOR

FIELD

The present application relates to methods for detecting exhaust gas sensor degradation.

BACKGROUND AND SUMMARY

An exhaust gas sensor may be positioned in an exhaust system of a vehicle to detect an air-fuel ratio of exhaust gases exiting an internal combustion engine of the vehicle. Exhaust gas sensor readings may be used to control operation of the internal combustion engine to propel the vehicle. Specifically, fuel injection amounts to the cylinders can be adjusted in response to the detected air-fuel ratio. Degradation of an exhaust gas sensor may result in increased emissions and/or reduced vehicle drivability. Accordingly, accurate determination of sensor degradation particularly prior to delivering the vehicle for road operation may provide enhanced engine operation.

The inventors herein have recognized the above issues and identified approaches to at least partly address the issues. In one example, a method comprises categorizing each respective concentration of a plurality of exhaust gas constituents measured by a gas analyzer into one of oxidants or reductants, the gas analyzer receiving exhaust gas flow from an engine. The method also includes determining an exhaust air-fuel ratio based on the categorized concentrations and validating output from an exhaust gas sensor receiving exhaust gas flow from the engine based on the determined exhaust air-fuel ratio.

For example, an engine controller in a vehicle on a test bench and a gas analyzer may each communicate separately with a validation controller. The gas analyzer may measure the concentration of individual constituents of tailpipe emissions exiting the vehicle and transmit the individual constituent concentration data to the validation controller. These individual concentrations may be categorized into one of oxidants or reductants and a first air-fuel ratio may be determined by the validation controller based on the categorized constituents. This first air-fuel ratio may then be compared to an output (e.g., an air-fuel ratio) of an exhaust gas sensor exposed to exhaust gases within the vehicle exhaust system. The comparison may be made such that the first air-fuel ratio and the exhaust gas sensor output are time synchronized and therefore refer to the same portion of exhaust gas. Exhaust gas sensor degradation may be confirmed if a difference is detected between the two air-fuel ratios.

In this way, a degraded exhaust gas sensor may be detected prior to putting the vehicle into operation on the road. By determining individual concentrations of a plurality of exhaust constituents with a gas analyzer, a more accurate air-fuel ratio can be calculated, allowing a more robust determination of exhaust gas sensor degradation.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
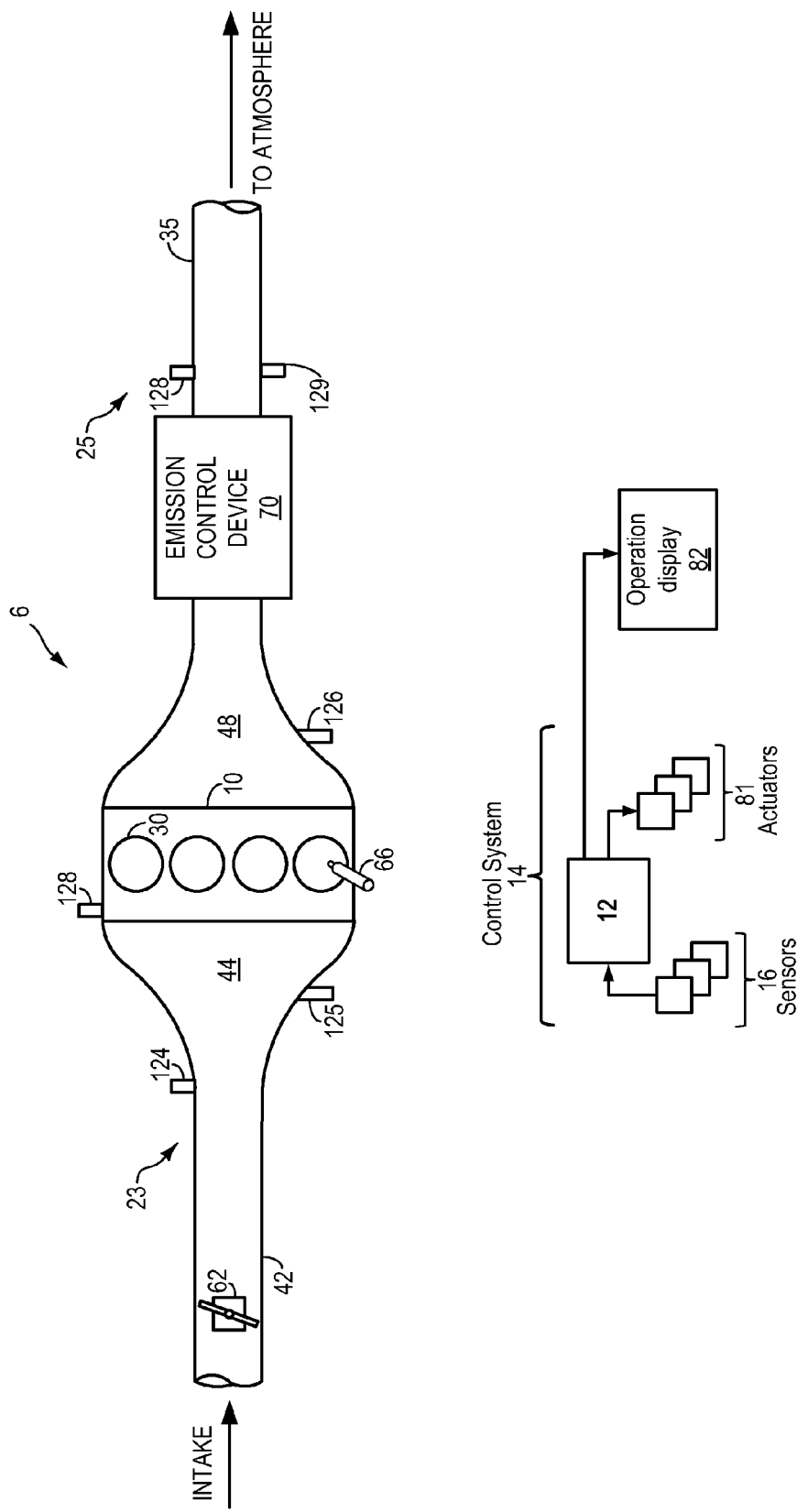
FIG. 1 schematically shows an example vehicle system.
Figure 2:
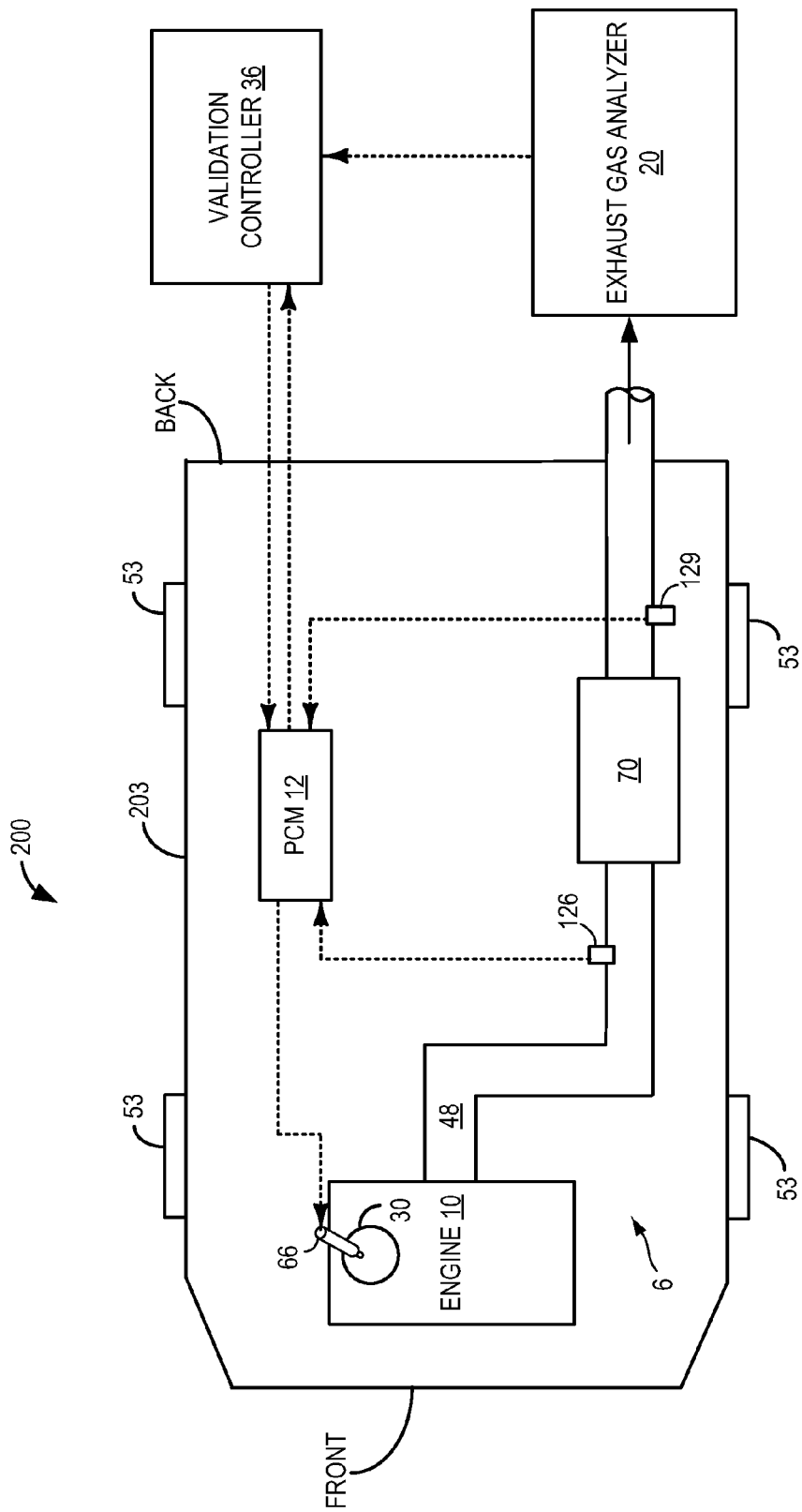
FIG. 2 illustrates a schematic diagnostic set up for the example vehicle system of FIG. 1.
Figure 3:
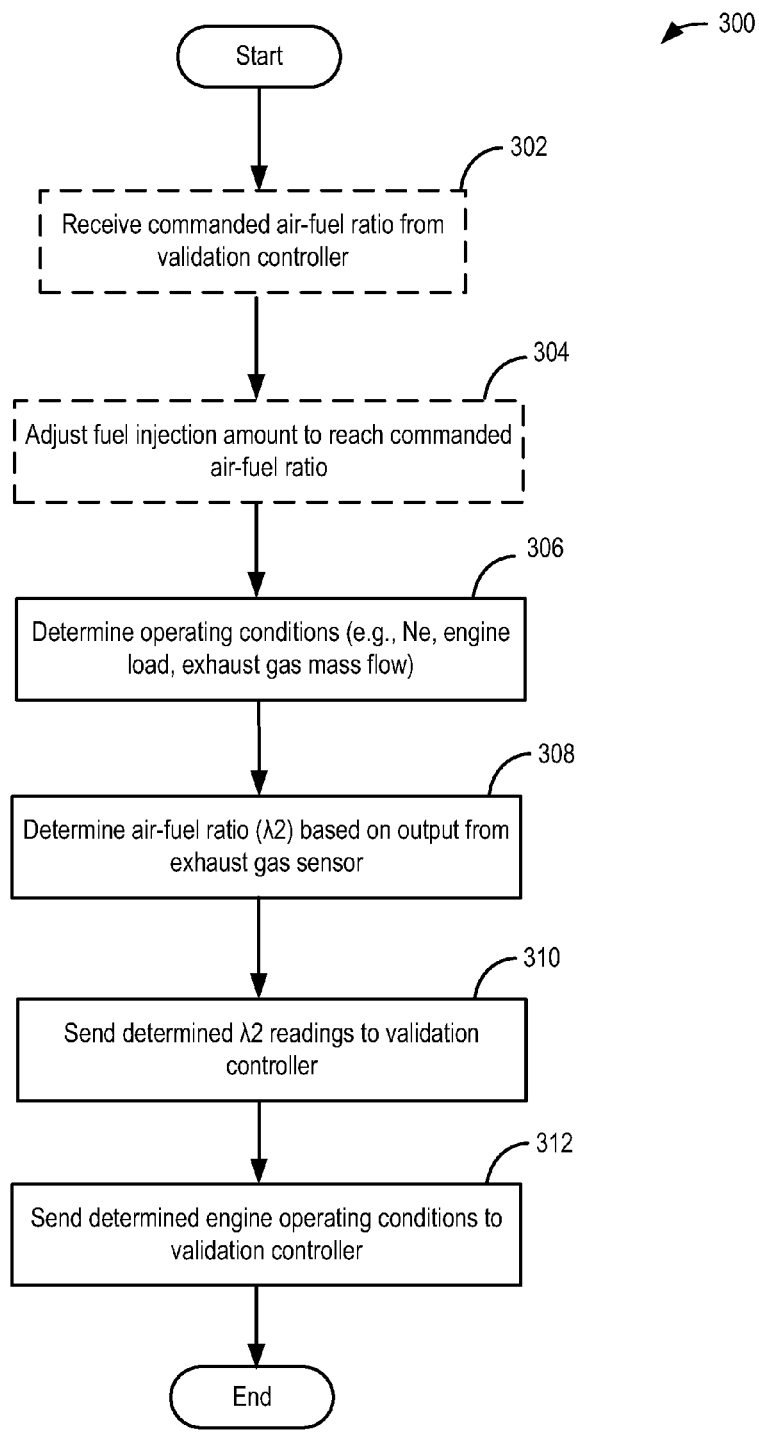
FIG. 3 is a flow chart illustrating an example method for an engine controller according to an embodiment of the present disclosure.
Figure 4:
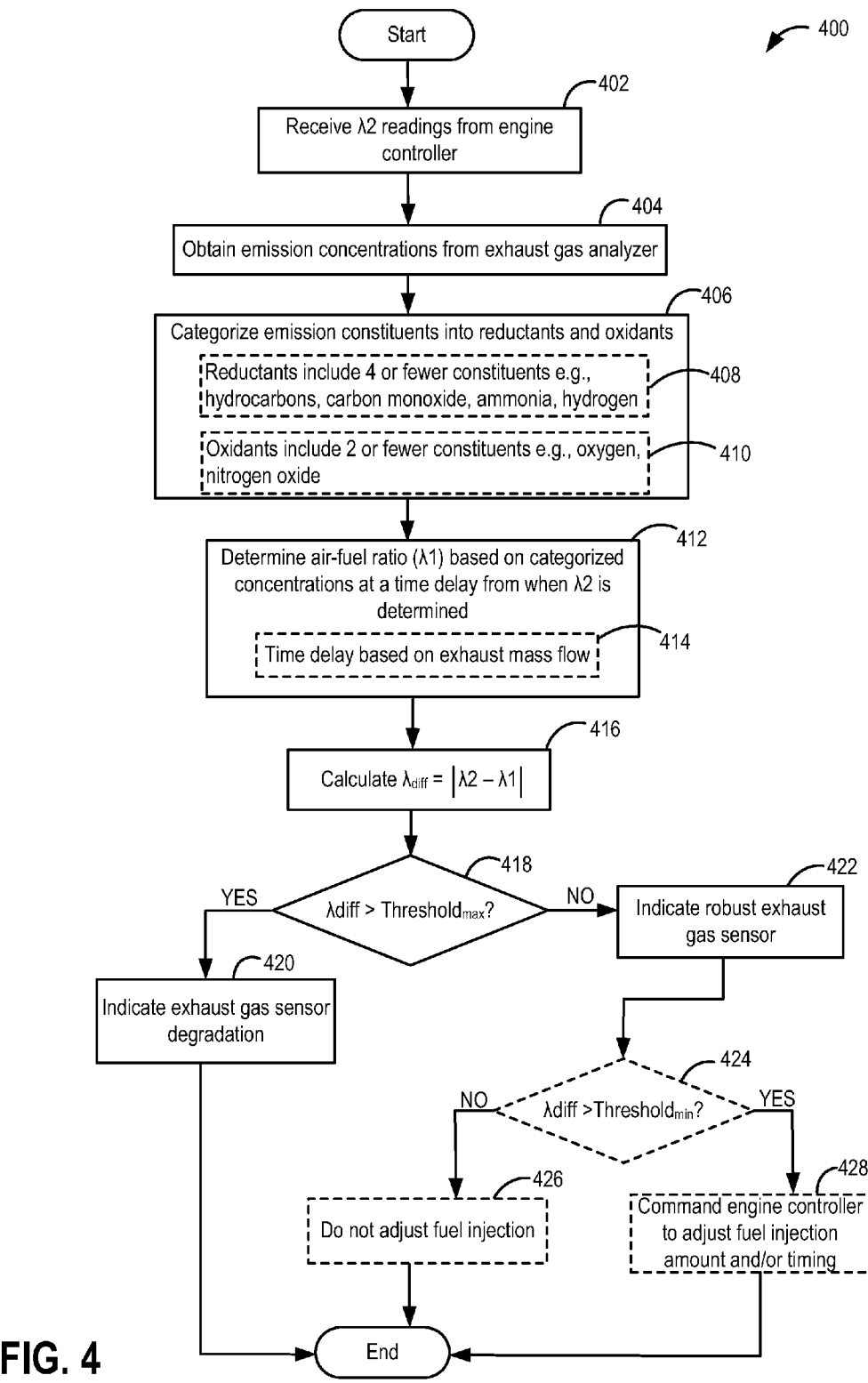
FIG. 4 is a flow chart depicting an example method for a validation controller according to an embodiment of the present disclosure.

Exhaust gas sensors may be provided in an exhaust passage of a vehicle, such as that shown in FIGS. 1 and 2, to determine the air-fuel ratio in exhaust gases exiting an engine. Prior to operating the vehicle on-road, exhaust gas sensors may be diagnosed for degradation by evaluating their performance on a test bench. Herein, the engine may be operated at a specific air-fuel ratio and an exhaust air-fuel ratio may be determined from the output of the exhaust gas sensor by the engine controller (FIG. 3). As the engine continues to operate at a specific air-fuel ratio, emissions from the tailpipe may be fed into a gas analyzer that is coupled to a validation controller. Concentrations of emission constituent species, such as oxygen ($O_2$), hydrogen ($H_2$), carbon monoxide (CO), hydrocarbons (HC), nitrogen oxide (NO), and ammonia ($NH_3$) may be measured by the gas analyzer and transferred to the validation controller. A second exhaust air-fuel ratio may be determined by the validation controller by categorizing the species into reductants and oxidants. By comparing the air-fuel ratio determined by the validation controller based on constituent concentrations with the air-fuel ratio determined from the exhaust gas sensor output, degradation in the exhaust gas sensor may be detected (FIG. 4).

FIG. 1 shows a schematic depiction of a vehicle system 6. The vehicle system 6 includes an engine 10 having a plurality of cylinders 30. The engine 10 includes an intake 23 and an exhaust 25. The intake 23 includes a throttle 62 fluidly coupled to the engine intake manifold 44 via an intake passage 42. The exhaust 25 includes an exhaust manifold 48 leading to an exhaust passage 35 that routes exhaust gas to the atmosphere. The exhaust 25 may include one or more emission control devices 70, which may be mounted in a close-coupled position in the exhaust. One or more emission control devices may include a three-way catalyst, lean NOx trap, diesel or gasoline particulate filter, oxidation catalyst, etc. It can be appreciated that other components may be included in the engine such as a variety of valves and sensors.

Engine 10 may receive fuel from a fuel system (not shown) including a fuel tank and one or more pumps for pressurizing fuel delivered to the injectors 66 of engine 10. While only a single injector 66 is shown, additional injectors are provided for each cylinder. It can be appreciated that the fuel system may be a returnless fuel system, a return fuel system, or various other types of fuel system. The fuel tank may hold a plurality of fuel blends, including fuel with a range of alcohol concentrations, such as various gasoline-ethanol blends, including E10, E85, gasoline, etc., and combinations thereof.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust gas sensor 126 (such as a linear UEGO sensor) located upstream of the emission control device, temperature sensor 128, and downstream exhaust gas sensor 129 (such as a binary HEGO sensor). Other sensors such as pressure, temperature, and composition sensors may be coupled to various locations in the vehicle system 6, as discussed in more detail herein. An estimate of the manifold airflow (MAF) may be obtained from MAF sensor 125 coupled to intake manifold 44, and communicated with controller 12. Alternatively, MAF may be inferred from alternate engine operating conditions, such as mass air pressure (MAP), as measured by a MAP sensor 124 coupled to the intake manifold 44.

In one example, an actuator may include a "message center" including an operation display 82 where, in response to an indication of exhaust gas sensor degradation, a message may be output to a vehicle operator indicating a need to replace the sensor, for example. As another example, the actuators may include fuel injector 66, and throttle 62. The control system 14 may include an engine controller 12. The controller may receive input data from the various sensors, process the input data, and trigger the actuators in response to the processed input data based on instructions or code programmed therein corresponding to one or more routines. Example control routines are described herein with regard to FIGS. 3-4.

Exhaust gas sensors 126 and 129 may be diagnosed for degradation by testing the vehicle system of FIG. 1 on bench as depicted in FIG. 2. A vehicle 200 is depicted in FIG. 2 and includes a vehicle body 203 with a front end, labeled "FRONT", and a back end labeled "BACK." Vehicle 200 may include a plurality of wheels 53. Engine 10 is shown with a plurality of cylinders 30 with each cylinder being fueled by a fuel injector 66. As such, vehicle and engine components previously introduced in FIG. 1 are numbered similarly in FIG. 2 and not reintroduced.

Gas analyzer 20 may receive exhaust gas from vehicle 200 via a probe (not shown). Gas analyzer 20 may be an infrared gas analyzer wherein constituent gases within an exhaust gas sample are determined based on their absorption of a specific wavelength in an emitted infrared light. A gas analyzer may measure concentrations of a range of species including in some examples, 4 species, 5 species, or more. These species could include one or more of $H_2$, CO, NO, HC, $NH_3$, and $O_2$. By using a gas analyzer to measure concentrations of individual species, a more accurate and reliable determination of air-fuel ratio may be possible.

Gas analyzer 20 is illustrated as located remotely from vehicle 200 and receiving tailpipe emissions (e.g., from the end of the tailpipe) which may be representative of emissions that have exited emissions device 70. With this set-up, the robustness of exhaust gas sensor 129 may be monitored. In another example, gas analyzer 20 may receive exhaust gases from a pre-emissions device tap. Herein, exhaust gases from upstream of emissions device 70 may be analyzed and used to diagnose exhaust gas sensor 126 located upstream of emissions device 70.

As depicted in FIG. 2, gas analyzer 20 may be connected to a validation controller 36. Validation controller 36 may be located remotely from vehicle 200. In one example, validation controller 36 may be a computer including a processor configured to receive and process input data, and execute non-transitory instructions stored in its memory. Validation controller 36 may also communicate with and receive data from engine controller 12. Thus, validation controller 36 is operatively coupled to engine controller 12 and gas analyzer 20.

In this way, validation controller 36 may command engine controller 12 to operate engine 10 at a given air-fuel ratio and receive feedback from engine controller 12 related to an output from an exhaust gas sensor in the exhaust system of engine 10. Likewise, validation controller 36 may receive a plurality of exhaust gas constituent concentrations from gas analyzer 20. Each of the said exhaust gas constituent concentrations may be categorized by validation controller 36 into aggregate reductants or oxidants. Based on the range of constituents that gas analyzer 20 may measure, the reductant group may comprise four or fewer species and the oxidant group may comprise two or fewer species. An air-fuel ratio may be determined based on these categories of oxidants and reductants, as will be described in reference to FIG. 4.

FIG. 3 is a flow chart illustrating a method 300 for an engine controller operating an exhaust gas sensor evaluation according to this disclosure. Specifically, the engine controller may operate the engine at a given air-fuel ratio and monitor output from an exhaust gas sensor which may be transmitted to a validation controller. Method 300 may be carried out by an engine controller, such as engine controller 12 of FIGS. 1 and 2.

At 302, the engine controller optionally receives a commanded air-fuel ratio from the validation controller. The commanded air-fuel ratio may be a specific air-fuel ratio to be used during engine operation. Consequently, at 304, the engine controller optionally adjusts a fuel injection amount to provide the commanded air-fuel ratio. In another example, steps 302 and 304 may be dispensed with and the engine controller may adjust engine air-fuel ratio according to instructions stored on the engine controller and not according to an engine air-fuel ratio commanded by the validation controller.

At 306, method 300 includes determining engine operating conditions. Conditions may include engine speed (Ne), engine load, exhaust gas mass flow, and other conditions. Exhaust gas mass flow may be determined in order to ensure a time synchronization between the exhaust gas sensor and the gas analyzer so that they sample the same portions of exhaust. Exhaust gas mass flow may be measured directly, or it may be estimated based on engine speed and load.

Next at 308, method 300 determines an exhaust air-fuel ratio, $\lambda 2$, based on an output from an exhaust gas sensor. In one example, with a set-up as depicted in FIG. 2 wherein the gas analyzer samples exhaust from the tailpipe, output from an exhaust gas sensor placed downstream of emissions device may be used to determine $\lambda 2$. In another example wherein the gas analyzer samples exhaust gases from upstream of the emissions device, output from an exhaust gas sensor placed upstream of said emissions device may be used to determine $\lambda 2$. At 310, the determined air-fuel ratio, $\lambda 2$, is transmitted by the engine controller to the validation controller. Multiple $\lambda 2$ readings may be obtained and transmitted to the validation controller to ensure reliability of data. At 312, the engine controller further transmits engine operating conditions data to the validation controller. As explained earlier, these conditions may include an exhaust gas mass flow, engine speed, etc. Method 300 may be repeated to gather air-fuel ratio ($\lambda 2$) readings based on the output of an exhaust gas sensor at a variety of commanded air-fuel ratios.

Turning now to FIG. 4, it portrays a flow chart for an example method 400 for a validation controller according to this disclosure. Specifically, a validation controller may receive concentrations of individual gas species from a gas analyzer which may be used to calculate a first air-fuel ratio which is then compared with an air-fuel ratio (λ2) determined from an exhaust gas sensor to detect exhaust gas sensor degradation. Method 400 may be carried out by a validation controller, such as validation controller 36 of FIG. 2.

At 402, method 400 includes receiving air-fuel ratio (λ2) readings from an engine controller, such as engine controller 12 of FIGS. 1 and 2. The engine controller may determine an air-fuel ratio, λ2, based on output from an exhaust gas sensor as described above with respect to FIG. 3. At 404, the validation controller obtains individual concentrations of a variety of exhaust species from a gas analyzer, such as gas analyzer 20 of FIG. 2. These species may include one or more of oxygen ($O_2$), hydrogen ($H_2$), carbon monoxide (CO), hydrocarbons (HC), nitrogen oxide (NO), and ammonia ($NH_3$).

At 406, the validation controller categorizes these exhaust species based on their chemical properties into two groups: oxidants and reductants. For example, reductants may include HC, CO, $H_2$, and $NH_3$ while the oxidant group may contain $O_2$ and NO. As shown at 408, the reductant group may include fewer than four species, e.g., HC, CO and $H_2$. As shown at 410, the oxidant group may comprise fewer than two species, e.g., $O_2$.

At 412, the validation controller determines a first air-fuel ratio (λ1) based on the categorized concentrations. The first air-fuel ratio (λ1) may be calculated from the categorized oxidants and reductants as follows:

$$\text{Cumulative reductant } [A] = \left(2 + \frac{y}{2}\right)[CH_y] + [CO] + [H_2] + [NH_3] \quad (1)$$

$$\text{Cumulative oxidant } [O_2]_{\mathit{eff}} = [O_2] + \frac{1}{2}[NO] \quad (2)$$

$$\text{Air-fuel ratio } [\lambda 1] = \left(\frac{2[O2]\mathit{eff} + 0.39}{[A] + 0.39}\right) \quad (3)$$

Equation 3, shown above, determines air-fuel ratio λ1 using a reduced number of species in comparison to the standard species utilized in typical air-fuel ratio determinations. Categorizing the species according to their chemical properties into reductants and oxidants (as shown at equations 1 and 2) may enable an air-fuel ratio calculation (as shown at equation 3) that is computationally less intensive. An air-fuel ratio calculated according to equation 3 may also be more accurate than typical air-fuel determinations from individual gas species.

First air-fuel ratio λ1 is determined at a time delay from when λ2 is determined by the engine controller in method 300. As shown at 414, the time delay may be based on a measurement of exhaust gas mass flow received from the engine controller at step 312 of method 300. Alternatively or additionally, exhaust gas mass flow may be determined based on the received engine speed and load. At 416, the validation controller compares the first air-fuel ratio (λ1) obtained from species categorization with air-fuel ratio λ2 determined from an exhaust gas sensor output at step 308 of method 300. A difference between the two readings, λdiff, is calculated at 416 as an absolute number. At 418, the absolute λdiff is compared to a threshold, e.g., $\text{Threshold}_{max}$. In one example, $\text{Threshold}_{max}$ may be a difference of 5%. In another example, $\text{Threshold}_{max}$ may be a difference of 10%. $\text{Threshold}_{max}$ may be a smaller difference of 5% if the operator determines that a brand new exhaust gas sensor included in a vehicle before on-road operation should perform at industry standards. Alternatively, a larger difference of 10% may be acceptable if the operator determines that a fuel injection adjustment may be used to maintain a determined air-fuel ratio. However, the above example thresholds are non-limiting, as other thresholds are possible.

If the absolute λdiff is greater than $\text{Threshold}_{max}$, a degraded sensor is indicated at 420. If a degraded sensor is detected, an operator of the vehicle may be instructed to replace the exhaust gas sensor in order to provide the vehicle with a healthy exhaust gas sensor for road operation. On the other hand, if the absolute λdiff is lower than $\text{Threshold}_{max}$, a robust exhaust gas sensor is determined and indicated at 422. Thus, an exhaust gas sensor may be deemed robust when the air-fuel ratio (λ2) determined from an output of said exhaust gas sensor is the same as the air-fuel ratio (λ1) calculated from individual gas concentrations in the emissions.

In some examples, method 400 may end after step 422. However, in other examples, method 400 may perform an additional check at 424 by comparing λdiff with a different, lower threshold, e.g. $\text{Threshold}_{min}$. In one example, $\text{Threshold}_{min}$ may be 2% if the $\text{Threshold}_{max}$ difference at step 418 is 5%. Alternatively, $\text{Threshold}_{min}$ may be 5% if a $\text{Threshold}_{max}$ difference of 10% has been utilized at step 418. These example thresholds are non-limiting, as other thresholds are possible.

If λdiff is greater than $\text{Threshold}_{min}$, the engine controller may be commanded to adjust a fuel injection amount or timing at 428 to compensate for the smaller difference in air-fuel ratios before method 400 ends. If λdiff is lower than $\text{Threshold}_{min}$, method 400 does not adjust fuel injection and ends. The optional check at 424 may be performed to update information stored on the engine controller (e.g., look-up tables) that correlate exhaust air-fuel ratio and engine air-fuel ratio, due to small differences in the air-fuel ratios λ1 and λ2.

While the embodiments discussed above with respect to FIGS. 3 and 4 diagnose an exhaust gas sensor positioned downstream of an emissions control device via a gas analyzer receiving exhaust from a vehicle tailpipe, in some embodiments an exhaust gas sensor upstream of the emissions control device may also be diagnosed by the gas analyzer. However, the exhaust air-fuel ratio determined based on output from the gas analyzer may be adjusted to account for activity of the emissions control device. For example, the emissions control device may convert one or more exhaust gas constituents (e.g., hydrocarbons or NOx), resulting in a lower concentration of those constituents at the gas analyzer than would be present in the exhaust upstream of the emissions control device. Accordingly, the exhaust air-fuel ratio may be adjusted based on exhaust temperature, oxygen storage capacity, or other factors that impact catalyst activity.

Thus, the methods 300 and 400 presented above with respect to FIGS. 3 and 4 provide a method for diagnosing an exhaust gas sensor in the exhaust system of an engine. The method comprises using a validation controller to command an engine controller to operate an engine at a given air-fuel ratio and receiving, from the engine controller, a first exhaust air-fuel ratio determined based on output from an exhaust gas sensor receiving exhaust gas from the engine. Additionally, the validation controller determines a second exhaust air-fuel ratio based on output from a gas analyzer receiving exhaust gas from the engine wherein the output from the gas analyzer includes a plurality of exhaust gas constituent concentrations categorized into either a reductant group or an oxidant group. Further, the second exhaust air-fuel ratio is determined at a time delayed from when the first exhaust air-fuel ratio is determined. The validation controller indicates degradation of the exhaust gas sensor based on the first exhaust air-fuel ratio and the second air-fuel ratio.

In this way, an exhaust gas sensor within a vehicle may be diagnosed prior to putting the vehicle on-road. By using a gas analyzer to determine exhaust gas constituent concentrations, a more reliable air-fuel ratio may be estimated. By comparing an output of an exhaust gas sensor to the air-fuel ratio determined from exhaust gas constituent concentrations, a more accurate detection of degradation may be made. Overall, emissions may be controlled and drivability may be enhanced.

Note that the example control and estimation routines included herein can be used with various engine and/or vehicle system configurations. The control methods and routines disclosed herein may be stored as executable instructions in non-transitory memory. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
   measuring respective concentrations of a plurality of exhaust gas constituents with a gas analyzer receiving exhaust gas flow from an engine, and categorizing each constituent into either an oxidant group or a reductant group;
   determining a first exhaust air-fuel ratio based on the measured concentrations; and
   validating a second exhaust air-fuel ratio output from an exhaust gas sensor receiving exhaust gas flow from the engine based on the first exhaust air-fuel ratio,
   wherein the gas analyzer is located remotely from a vehicle in which the engine and exhaust gas sensor are installed.

2. The method of claim 1, wherein categorizing each constituent measured by the gas analyzer comprises categorizing each of oxygen, hydrocarbons, carbon monoxide, nitrogen oxide, hydrogen, and ammonia into either the oxidant group or the reductant group.

3. The method of claim 1, wherein the determination of the first exhaust air-fuel ratio is further based on engine operating conditions.

4. The method of claim 3, wherein the engine operating conditions include engine speed, engine load, and exhaust gas mass flow.

5. The method of claim 4, wherein the output from the exhaust gas sensor and measurements of engine speed, engine load, and exhaust gas mass flow are each received from a controller of the engine.

6. The method of claim 1, wherein validating the second exhaust air-fuel ratio based on the first exhaust air-fuel ratio further comprises comparing the second exhaust air-fuel ratio to the first exhaust air-fuel ratio, and if the second exhaust air-fuel ratio differs from the first exhaust air-fuel ratio by more than a threshold amount, indicating degradation of the exhaust gas sensor.

7. The method of claim 1, further comprising calculating a cumulative reductant based on the measured concentrations of the constituents in the reductant group and calculating a cumulative oxidant based on the measured concentrations of the constituents in the oxidant group, wherein the determination of the first exhaust air-fuel ratio is based on the cumulative reductant and the cumulative oxidant.

8. The method of claim 1, wherein the gas analyzer is an infrared gas analyzer, and wherein constituent gases within an exhaust gas sample are determined based on their absorption of a specific wavelength in an emitted infrared light.

9. A system, comprising:
   an engine coupled to an exhaust system;
   an exhaust gas sensor positioned in the exhaust system;
   an engine controller to receive output from the exhaust gas sensor;
   a gas analyzer receiving exhaust gas flow from the exhaust system; and
   a validation controller operatively coupled to the gas analyzer and the engine controller, and including instructions to:
   categorize each of a plurality of exhaust gas constituents into either an oxidant group or a reductant group;
   measure respective concentrations of the constituents with the gas analyzer;
   calculate a cumulative reductant based on the concentrations of the constituents in the reductant group;
   calculate a cumulative oxidant based on the concentrations of the constituents in the oxidant group;
   determine a first exhaust air-fuel ratio based on the cumulative reductant and the cumulative oxidant;
   compare the first exhaust air-fuel ratio to a second exhaust air-fuel ratio received from the engine controller, the second exhaust air-fuel ratio determined by the engine controller from the output from the exhaust gas sensor; and if the first exhaust air-fuel ratio differs from the second exhaust air-fuel ratio by more than a threshold amount, indicate degradation of the exhaust gas sensor.

10. The system of claim 9, further comprising a vehicle in which the engine, exhaust system, exhaust gas sensor, and engine controller are each installed, and wherein the gas analyzer and validation controller are located remotely from the vehicle.

11. The system of claim 9, wherein the validation controller includes further instructions to determine the first exhaust air-fuel ratio time delayed from when the second exhaust air-fuel ratio is determined, the time delay based on a measurement of exhaust gas mass flow received from the engine controller.

12. The system of claim 9, wherein the validation controller includes further instructions to command the engine controller to operate the engine at a given engine air-fuel ratio before the second exhaust air-fuel ratio is determined.

13. The system of claim 9, wherein the reductant group includes four or fewer exhaust gas constituents.

14. The system of claim 13, wherein the reductant group includes one or more of hydrocarbons, carbon monoxide, hydrogen, and ammonia.

15. The system of claim 9, wherein the oxidant group includes two or fewer exhaust gas constituents.

16. The system of claim 15, wherein the oxidant group includes one or more of oxygen and nitrogen oxide.

17. A method, comprising:
sending a command to an engine controller to operate an engine at a given air-fuel ratio;
receiving, from the engine controller, a first exhaust air-fuel ratio determined based on an output from an exhaust gas sensor receiving exhaust gas from the engine;
determining a second exhaust air-fuel ratio based on an output from a gas analyzer receiving exhaust gas from the engine, the gas analyzer located remotely from a vehicle in which the engine and the exhaust gas sensor are installed, the output from the gas analyzer including respective concentrations of a plurality of exhaust gas constituents, each constituent categorized into either a reductant group or an oxidant group, the second exhaust air-fuel ratio determined at a time delayed from when the first exhaust air-fuel ratio is determined; and
indicating degradation of the exhaust gas sensor based on the first exhaust air-fuel ratio and the second exhaust air-fuel ratio.

18. The method of claim 17, wherein indicating degradation of the exhaust gas sensor comprises, if the first exhaust air-fuel ratio differs from the second exhaust air-fuel ratio by more than a threshold amount, indicating the exhaust gas sensor is degraded.

19. The method of claim 18, further comprising, if the first exhaust air-fuel ratio differs from the second exhaust air-fuel ratio by more than the threshold amount but less than a second threshold amount, sending a command to the engine controller to adjust a fuel injection amount and/or timing based on the indicated exhaust gas sensor degradation.

* * * * *